United States Patent
Herold et al.

[11] Patent Number: 5,167,448
[45] Date of Patent: Dec. 1, 1992

[54] MIXING APPARATUS FOR PASTES

[75] Inventors: Wolf-Dietrich Herold, Seefeld; Peter Koran, Weilheim, both of Fed. Rep. of Germany

[73] Assignee: Thera Patent GmbH & Co., Seefeld, Fed. Rep. of Germany

[21] Appl. No.: 538,330

[22] Filed: Jun. 15, 1990

[30] Foreign Application Priority Data

Jun. 15, 1989 [DE] Fed. Rep. of Germany ....... 8907335

[51] Int. Cl.$^5$ .............................................. B01F 11/00
[52] U.S. Cl. .................................... 366/213; 366/217; 494/19; 494/84
[58] Field of Search ............... 366/208, 209, 213, 214, 366/217, 220, 227, 228, 287, 288, 235; 494/19, 33, 52, 84; 241/175, 123; 475/182, 311; 222/386

[56] References Cited

U.S. PATENT DOCUMENTS

| 1,144,272 | 6/1915 | West | 366/235 |
|---|---|---|---|
| 1,578,067 | 1/1925 | Bonoff | 366/208 |
| 1,774,257 | 8/1930 | English | 366/217 |
| 2,443,593 | 6/1944 | Birsch | 494/84 |
| 3,170,648 | 2/1965 | McShirley | 241/284 |
| 3,562,962 | 2/1971 | Ohno | 366/235 |
| 3,679,184 | 7/1972 | Woodham | 366/219 |
| 3,684,136 | 8/1972 | Baumann | 206/219 |
| 3,848,796 | 11/1974 | Bull | 494/84 |
| 3,880,408 | 4/1975 | Karjalainen | 366/217 |
| 3,882,716 | 5/1975 | Bieman | 494/19 |
| 4,129,249 | 12/1978 | Todd | 494/84 |
| 4,131,369 | 12/1978 | Gordon et al. | 366/146 |
| 4,497,581 | 2/1985 | Miller | 366/208 |
| 4,515,267 | 5/1985 | Welsh | 206/219 |
| 4,540,397 | 9/1985 | Lolachi et al. | 494/84 |
| 4,710,161 | 12/1987 | Takabayashi et al. | 494/84 |

FOREIGN PATENT DOCUMENTS

| 0178780 | 6/1954 | Fed. Rep. of Germany | 494/33 |
|---|---|---|---|
| 2734488 | 2/1978 | Fed. Rep. of Germany | 366/279 |
| 3708442 | 3/1987 | Fed. Rep. of Germany . | |
| 976266 | 3/1951 | France . | |
| 94554 | 1/1972 | German Democratic Rep. . | |
| 58-15665 | 1/1983 | Japan . | |
| 59-97838 | 6/1984 | Japan . | |
| 59-129656 | 7/1984 | Japan . | |
| 633258 | 12/1949 | United Kingdom . | |

Primary Examiner—Philip R. Coe
Assistant Examiner—Tony Soohoo
Attorney, Agent, or Firm—Foley & Lardner

[57] ABSTRACT

A mixing apparatus for pastes comprises a mount (18) for a mixing container (19) supported on a rotor (10) for rotation relative to the rotor about an axis (16) which is eccentric with respect to the rotor axis (15). During a mixing phase, a transmission (20 . . . 22) causes the mount (18) to rotate about its eccentric axis (16) so that the mixing container (19) executes an overall circulatory reciprocation and the container contents (29) are subjected to a shaking motion. For a subsequent compression phase, the transmission (20 . . . 22) is switched-over while the rotor (10) continues to rotate, so that the mount (18) is now free to assume an orientation that is fixed with respect to the rotor (10) and in which the mixed paste is forced against a dispensing piston (55) provided in the container (19) and is thereby degassed.

16 Claims, 2 Drawing Sheets

MIXING APPARATUS FOR PASTES

BACKGROUND OF THE INVENTION

When a paste is mixed from two or more components, specifically a liquid and a powdery component for producing a bone cement, it is essential for the mixture to be made as homogeneous as possible and to be completely free of bubbles to obtain a high strength after setting. To this end, any air included during the mixing process must be subsequently removed. If the product is a bone cement having a typical setting time of several minutes, only short time is available for preparing the mixture and removing the air.

German Offenlegungsschrift 3,708,442 discloses a mixing apparatus for pastes which comprises a rotor rotatable about a first axis and including a mount for receiving a mixing container which holds the components of the paste to be prepared, the mount being supported on the rotor for rotation about a second axis eccentric with respect to the first axis, and a transmission for causing the mount to rotate about the second axis while the rotor rotates about the first axis.

In the known device, the components to be mixed are contained in a common container and are separated in a transport condition of the container by a partitioning wall. In use, the partitioning wall is first of all ruptured, and the container is inserted into the mount of the mixing apparatus. Resilient means retain the mount relative to a base of the apparatus in such a manner that, while the rotor rotates, the general orientation of the mount is maintained, so that the container accommodated in the mount is subjected to a circular reciprocating motion. Upon termination of the mixing process, the container is connected to a vacuum pump to degas the mixture. Thereafter, the container is connected to a dispensing device in which a plunger acts on a piston located at one end of the container to dispense the finished mixture through a dispensing opening provided at the other end of the container.

Similar mixing apparatus are described in U.S. Pat. No. 4,131,369 and East German Patent 94,554. In the former apparatus, the mixing container is mounted on a planet gear which meshes with the sun gear and the outer ring gear of an epicyclic gearing. By periodically changing the relative angular position between the sun and ring gears, the container is intermittently rotated back and forth by 180°.

Since the mixed paste has a highly viscous, kneadable consistency, particularly in case of a bone cement, air bubbles which may be entrapped during the mixing process can be removed only by an extremely high vacuum, if at all. During such evacuation, however, volatile constituents are also removed from the paste, which results in an unpredictable alteration of the mixing ratio of the cement and a deterioration of its chemical and physical properties.

SUMMARY OF THE INVENTION

It is an object of the invention to provide a mixing apparatus for pastes, particularly a bone cement, which is of uncomplicated design and easy to operate and which permits a quick preparation of a homogeneous and bubble-free mixture of a predetermined mixing ratio.

The invention meets this object by a mixing apparatus for pastes which comprises a rotor mounted for rotation about a first axis, a mount for receiving a mixing container holding components of the paste, the mount being supported on said rotor so as to be rotatable about a second axis eccentric with respect to the first axis, and transmission means for causing the mount to rotate about said second axis while the rotor rotates about the first axis, the transmission means being adapted to be switched-over to a condition in which it allows the mount to rotate freely about said second axis relative to the rotor.

The apparatus of the present invention is thus adapted to carry out two process steps, namely first mixing the starting components and subsequently compressing the mixture. In the mixing step, the mount holding the container rotates about its eccentric axis in such a manner that the components are exposed to a reciprocating shaking motion. By switching-over the transmission, the mount carrying the container becomes free to adjust itself to an orientation fixed relatively to the rotor, so that the contents of the container are then compressed by the centrifugal forces produced in the further rotation of the rotor.

The switching-over of the transmission may be done while the rotor continues to rotate, so that the compression step may immediately follow the mixing step, thereby minimizing the overall time required.

In a preferred embodiment, the arrangement is such that the center of gravity of the unit formed by the mount and the container received in the mount is situated between the second axis and a piston disposed therein, irrespective of the position of the container contents. This will cause the mount to adjust itself, at the beginning of the compression step, into an orientation, in which the piston is most remote from the rotor axis. The mixed paste will thus be compressed towards the piston and can be subsequently dispensed from the container by advancing the piston with no air being pressed through the paste during the dispensing action.

Further features of the invention relate to specifically uncomplicated embodiments of the transmission, to a clutch for switching-over the transmission between the mixing and compression steps, and to a remote control for the clutch.

Two or more mounts each for receiving a container may be equi-angularly spaced around the rotor. This may be of advantage if larger amounts of paste are required to be prepared simultaneously. In this embodiment, the rotor is dynamically balanced.

In a further embodiment, a timing circuit may be provided which provides a first adjustable period of time for the mixing step and a second adjustable period for the compression step, and which automatically switches the transmission from the mixing operation of the apparatus to the compressing operation.

The timing circuit may further provide an initial interval in which the mount carrying the container is freely rotatable about its second axis, just as in the final compression step, which initial phase is suitable for handling containers in which the initially separated component is transferred to a mixing chamber containing the powdery component by a force acting in the axial direction of the container.

Whenever switching over from one phase of operation to the next, the rotor speed may be adjusted to the value best suited for the respected function.

DETAILED DESCRIPTION OF PREFERRED EMBODIMENTS

Figure 1:
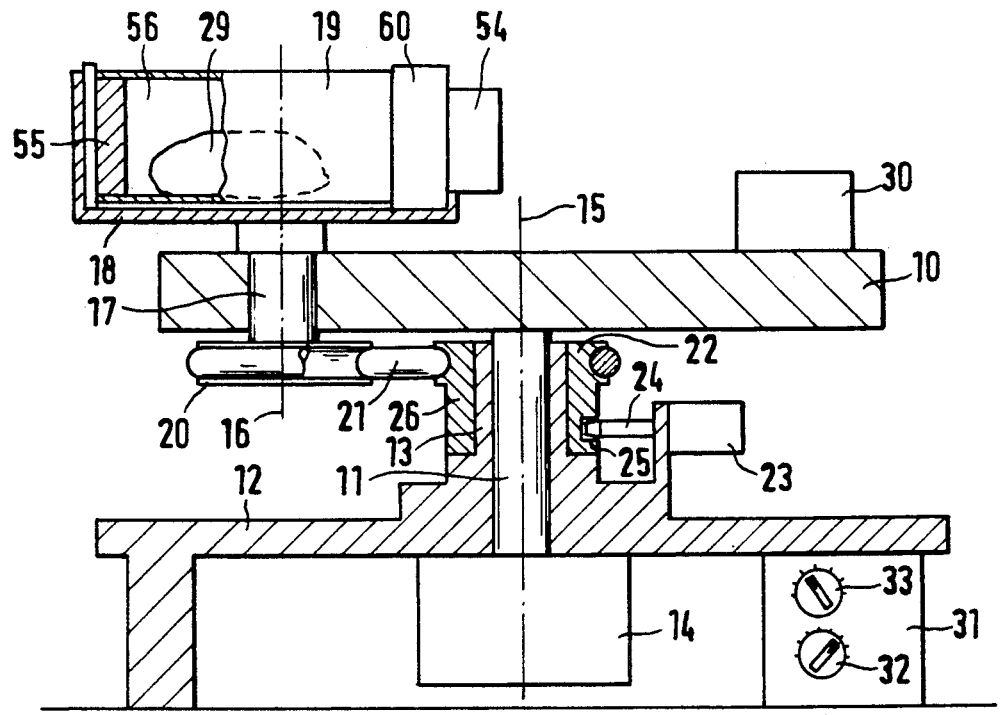
FIG. 1 is a schematic sectional view of a mixing apparatus taken along the rotor axis.

In the apparatus shown in FIG. 1, a rotor 10 is connected to a shaft 11 which is rotatably mounted in a bushing 13 fixed to a base 12 of the apparatus. The shaft 11 is driven by a motor 14 accommodated in the base 12.

A shaft 17 is mounted on the rotor 10 for rotation about an eccentric axis 16 which is parallel to the axis 15 of the rotor shaft 11. Above the rotor 10, the eccentric shaft 17 carries a mount 18 for receiving a mixing container 19, and a pulley 20 is fixed to the shaft 17 below the rotor 10. A further pulley 22 is mounted on the bushing 13 for rotation about the axis 15 of the rotor shaft 11 and is connected to the first pulley 20 by means of a driving belt 21.

A solenoid 23 is fixed to the base 12. A plunger 24 connected to the armature of the solenoid 23 is adapted to engage a recess 25 formed in the outer side of a downwardly extending sleeve portion 26 of the pulley 22.

The mixing container 19 includes a chamber 54 shown at the right in FIG. 1 for receiving a first component, which may be a liquid component of a bone cement, and a mixing chamber 56 shown at the left side in FIG. 1 for receiving a powdery component. The mixing chamber 56 has one end closed off by a-movable piston 55. In the initial condition of the container, the chambers 54, 56 are separated from each other by a locked valve-type seal (not shown). The seal may be unlocked by moving a ring 60 provided on the container 19 so that the liquid component can then be transferred to the mixing chamber 56 under the influence of a force acting in the direction of the mixing chamber.

The mount 18 and the container 19 are adapted to each other in such a manner that the container 19 may be inserted into the mount in only one predetermined orientation. Further, the mount 18 and the container 19 are configured so that the center of gravity of the unit formed by these two parts 18, 19 is offset from the axis 16 towards the piston 55, irrespective of the position of the container contents, which are indicated at 29 in FIG. 1.

A counterweight 30 is fixed to the rotor 10 at a location diametrically opposite the axis 16 to compensate for the unbalance formed by the mount 18, the shaft 19, the pulley 20, and the filled mixing container 19.

Figure 3:
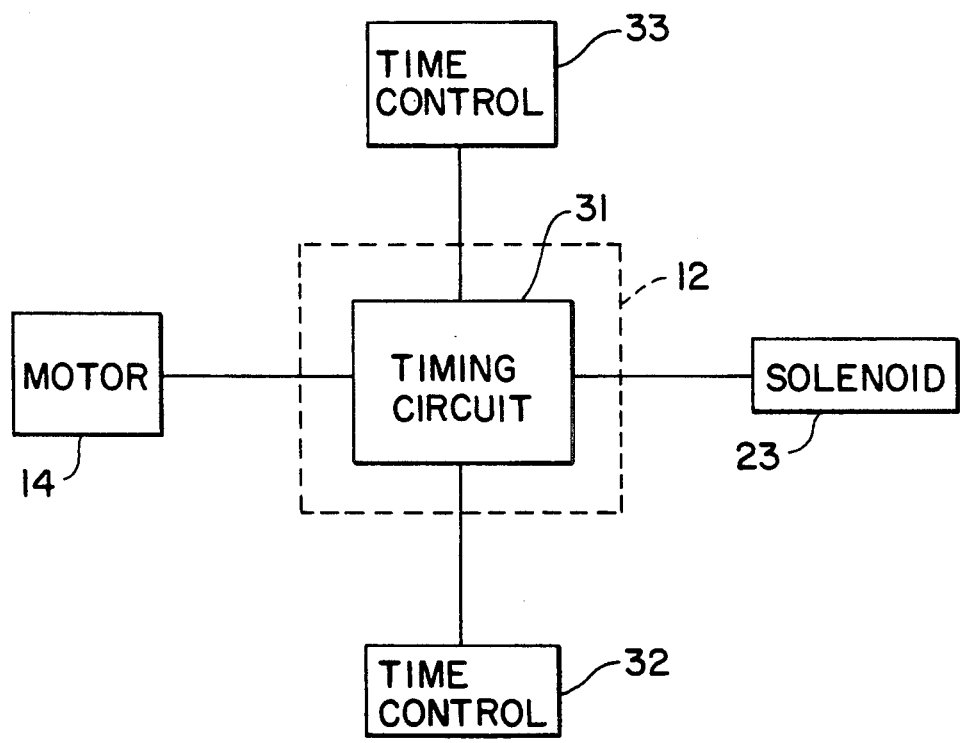
FIG. 3 is a schematic view of the timing circuit for operation control.

The motor 14 and the electromagnet 23 are controlled by a timing circuit 31 disposed in the base 12, the circuit 31 (see FIG. 3) including a control 32 for setting the operating period of the motor 14 and a control 33 for setting the actuation time of the solenoid 23.

In operation, the mixing container 19 is inserted into the mount 18 in the predetermined orientation after the ring 60 has been moved to a position in which the above-mentioned valve-type seal is unlocked.

The motor 14 is then actuated to rotate the rotor 10. During this first operating phase, the plunger 24 of the solenoid 23 is withdrawn from the recess 25 formed in the sleeve 26 so that the pulley 22 is freely rotatable about the bushing 13, and the mount 18 is free to rotate relative to the rotor 10. Irrespective of the initial position of the mount 18, centrifugal forces created by the rotation of the rotor 10 will cause the unit formed by the mount 18 and the container 19 to orient itself to a position relative to the rotor 10 in which the piston 55 is most remote from the axis 15. In this position, which is illustrated in FIG. 1, the mount 18 including the container 19 will be entrained with the rotor 10 without additional rotation about the axis 16, so that the liquid component is transferred from the chamber 54 to the mixing chamber 56.

By actuating the solenoid 23, the plunger 24 is extended to the position shown in FIG. 1 in which it engages the recess 25 formed in the sleeve 26, so that the pulley 22 is now kept stationary. Continued rotation of the rotor 10 about its axis 15 will consequently cause the mount 18 holding the container 19 to rotate about the axis 16 relative to the rotor 10.

If both pulleys 20 and 22 have equal diameters as has been assumed in FIG. 1, the container 19 is moved parallel to itself on a circle centered at the axis 15, so that the container contents 29 will perform a rolling or tumbling movement along the inner wall of the mixing chamber 56. The components will thereby be mixed thoroughly to form a homogeneous paste.

Upon expiry of the time period selected by the control 33, which period has been started with the first actuation of the solenoid 23 and has a duration dependent on the properties of the components to be mixed, the timing circuit 31 again actuates the solenoid 23 to retract the plunger 24. The mount 18 will thereby again become free to rotate about its axis 16 and will adjust itself to the orientation shown in FIG. 1, which is fixed relative to the rotor 10. In this phase, the container contents 29 will be forced against the piston 55 and compressed to expel any air that may have been included in the paste during the mixing step.

The rotor 10 will stop rotating upon expiry of the total time period set by means of the control 32. The container 19 is then removed from the mount 18, and the finished paste may be dispensed.

Figure 2:
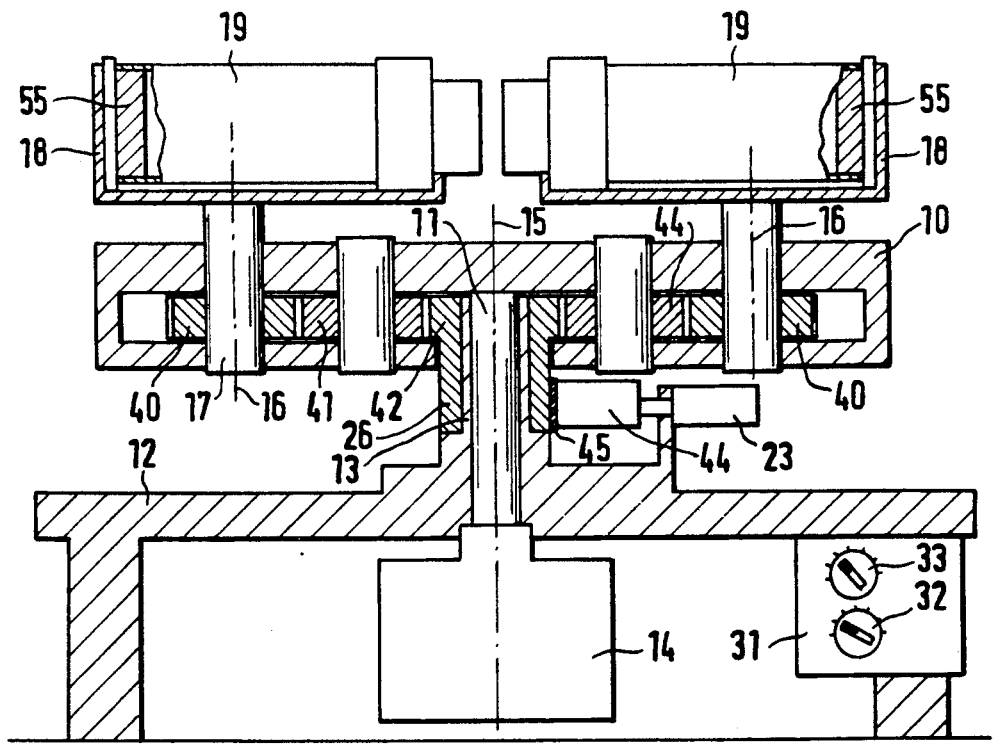
FIG. 2 is a view similar to FIG. 1 showing a modified embodiment of a mixing apparatus.

The apparatus shown in FIG. 2 differs from that of FIG. 1 in that a second mount 18 for receiving a second mixing container 19 is provided instead of the counterweight 30. More than two mounts each for receiving a mixing container may be disposed on the rotor 10 at positions equiangularly spaced around the axis 15.

In FIG. 2, the transmission which causes the mounts 18 to rotate relative to the rotor 10 during the mixing phase, includes toothed gears of which a central gear 42 is mounted for rotation about the stationary bushing 13 and meshes, via intermediate gears 41, with gears 40 fixed to shafts 17 of the container mounts 18.

The same kinematics as described with reference to FIG. 1 are obtained if the gears 40 and 42 have equal numbers of teeth. In case of different tooth numbers, the mounts 18 will not be guided parallel to themselves by the rotation of the rotor, but execute a rotation superimposed on the rotation of the rotor 10.

In the apparatus of FIG. 2, the clutch which keeps the central gear 42 stationary during the mixing phase is constituted by a brake. A brake shoe 44 is adapted to be actuated by a solenoid 23 and has a brake lining 45 cooperating with the outer peripheral surface of the sleeve portion 26 formed integrally with the central gear 42. This type of clutch is preferred over the embodiment of FIG. 1 in that it may be reengaged in any position of the central gear 42 to perform a subsequent mixing step.

As indicated in FIG. 2, the two mounts 18 are fixed to the shafts 17, which are coupled to each other via the gears 40 . . . 42, in such a way that when the clutch is disengaged both mounts 18 are allowed to adjust themselves to positions in which the piston 55 in each mixing container 22 is most remote from the rotor axis 15.

The above description has assumed that the rotor 18 rotates with constant speed throughout the three phases of operation (transfer of the liquid component to the mixing chamber 56—mixing—compression). Alternatively, the timing circuit 31 may be so designed that it provides a different motor speed for each phase. Specifically, the compression step may require a higher speed than the mixing step.

What is claimed is:

1. A mixing apparatus for pastes, comprising
a rotor mounted for rotation about a first axis,
a mount having a longitudinal axis and adapted to receive a mixing container holding components of the paste, said container being generally cylindrical and elongate and having a longitudinal axis, the mount being supported on said rotor so as to be rotatable about a second axis eccentric with respect to the first axis,
said mixing container including a piston disposed within said container at one end thereof for longitudinal movement to dispense paste from the container following mixing and removal of the container form the apparatus, said longitudinal axes of said mount and said container being substantially transverse to said first and second axes, and wherein the center of gravity of a unit constituted by said mount and said container inserted in the mount is disposed between said second axis and said piston irrespective of the position of the paste inside the container,
transmission means for causing the mount to rotate about said second axis while the rotor rotates about the first axis, and
means for switching said transmission means to a condition in which said mount is released so as to rotate freely about said second axis relative to the rotor.

2. The apparatus of claim 1, wherein said transmission means is adapted to be switched-over during the rotation of said rotor.

3. The apparatus of claim 1, wherein said transmission means includes a central wheel mounted for rotation about said first axis to cause said mount to rotate about said second axis, and clutch means which, when engaged, couples the central wheel to means causing a relative rotation between the central wheel and the rotor.

4. The apparatus of claim 3, further including a stationary base, and wherein said clutch means includes braking means which, when engaged, fixes the central wheel to said stationary base.

5. The apparatus of claim 3, wherein the central wheel is arranged to drive a further wheel connected to said mount via a belt.

6. The apparatus of claim 5, wherein the central wheel and said further wheel have equal diameters.

7. The apparatus of claim 3, wherein the central wheel is a gear which drives a further gear connected to said mount.

8. The apparatus of claim 7, wherein the central gear and said further gear have equal tooth numbers.

9. The apparatus of claim 3, including electromagnetic means for actuating said clutch means.

10. The apparatus of claim 1, wherein at least two mounts are disposed on said rotor at positions equiangularly spaced about said first axis.

11. A mixing apparatus for pastes, comprising
a rotor mounted for rotation about a first axis, and means for rotating said rotor,
a mount having a longitudinal axis and adapted to receive a generally cylindrical and elongate mixing container holding components of the paste, said container having a longitudinal axis, said mount being supported on said rotor so as to be rotatable about a second axis eccentric with respect to the first axis,
transmission means for causing the mount to rotate about said second axis while the rotor rotates about the first axis, the axes of said mount and said generally cylindrical container extending substantially transversely to said first and second axes, and
means for switching said transmission means to a condition in which said mount is released so as to rotate freely about said second axis relative to the rotor, said switching means including timing means for switching-over said transmission means upon expiry of a first adjustable period of rotor rotation, and for causing the rotor to continue rotating during a second adjustable period.

12. The apparatus of claim 11, wherein said timing means provides an initial phase of rotor rotation in which said mount is freely rotatable about said second axis, said first period being started at the end of said initial phase by switching said transmission means to a condition in which the mount is positively driven to rotate about said second axis.

13. The apparatus of claim 12, wherein said timing means includes means for varying the rotor speed when said transmission means is switched-over.

14. The apparatus of claim 11, wherein said transmission means is adapted to be switched-over during the rotation of said rotor.

15. The apparatus of claim 11, wherein said container includes a piston disposed at one end of said container, and wherein the center of gravity of a unit constituted by said mount and said container inserted in the mount is disposed between said second axis and said piston irrespective of the position of the paste inside said container.

16. The apparatus of claim 11, wherein said transmission means includes a central wheel mounted for rotation about said first axis to cause said mount to rotate about said second axis, and clutch means which, when engaged, couples said central wheel to means causing a relative rotation between said central wheel and said rotor.

* * * * *